United States Patent [19]

Knobloch et al.

[11]  4,396,552

[45]  Aug. 2, 1983

[54] NOVEL METAL MERCAPTIDES OF ESTERS OF β-MERCAPTOALKANOLS

[75] Inventors: Gerrit Knobloch, Lindenfels; Wolfgang Wehner, Zwingenberg; Hermann O. Wirth, Bensheim, all of Fed. Rep. of Germany

[73] Assignee: Ciba-Geigy Corporation, Ardsley, NY

[21] Appl. No.: 229,201

[22] Filed: Jan. 28, 1981

[30]     Foreign Application Priority Data

Feb. 8, 1980 [CH] Switzerland .................. 1036/80

[51] Int. Cl.$^3$ ................... C07F 7/22; C08H 3/00
[52] U.S. Cl. ..................... 260/429.7; 260/399; 260/414; 260/429 R; 260/429.3; 260/429.5; 260/429.9; 260/446; 560/51; 560/75
[58] Field of Search ............ 560/51, 75; 260/429.7, 260/446, 429 R, 429.9, 414, 429.3, 429.5, 448 AD, 399

[56]           References Cited

U.S. PATENT DOCUMENTS

| | | | |
|---|---|---|---|
| 3,281,455 | 10/1966 | Steinberg | 560/75 |
| 4,104,292 | 8/1978 | Dworkin | 260/429.7 |
| 4,122,064 | 10/1978 | Scheidl et al. | 260/429.7 X |
| 4,126,627 | 2/1978 | Reifenberg | 260/399 |
| 4,269,731 | 5/1981 | Mack | 260/429.7 |
| 4,279,806 | 7/1981 | Muldrow | 260/446 X |
| 4,287,118 | 9/1981 | Muldrow | 260/446 X |
| 4,303,578 | 12/1981 | Michaelis | 260/446 X |

FOREIGN PATENT DOCUMENTS 1948570  4/1970  Fed. Rep. of Germany .

*Primary Examiner*—Helen M. S. Sneed
*Attorney, Agent, or Firm*—Harry Falber

[57]               ABSTRACT

Metal mercaptides of the formula

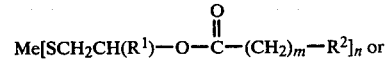

or

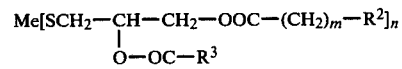

wherein Me is a metal, oxometal, alkoxymetal or organo-metal cation from the 1st–5th group of the periodic system, n is 0, 1 or 2, m is an integer from 1 to 4, $R^1$ is hydrogen, alkyl, acyloxymethyl or alkoxymethyl, $R^2$ is a sterically hindered phenol group, and $R^3$ is a monovalent organic radical, are stabilizers for organic materials which are sensitive to heat and oxygen. They can be used in particular as stabilizers for chlorine-containing thermoplasts, for elastomers and for lubricants. Preferred cations are organotin cations.

5 Claims, No Drawings

NOVEL METAL MERCAPTIDES OF ESTERS OF β-MERCAPTOALKANOLS

The invention relates to novel metal mercaptides of mercaptoalkanol esters of sterically hindered phenol (alkane)carboxylic acids, to a process for producing these metal mercaptides, and to their use as stabilisers for organic materials.

It is known that metal mercaptides, especially mono- and di-organotin mercaptides, are good thermostabilisers for PVC. Examples of these are dialkyltin-di(alkylthioglycolates), such as the compound $(C_8H_{17})_2Sn(SCH_2COO\text{-}i\text{-}C_8H_{17})_2$, which is obtainable commercially under the name of "Irgastab 17 MOK", or aliphatic carboxylic esters of dialkyltin-hydroxyethyl mercaptides, such as are disclosed in the U.S. Pat. No. 2,870,182, for example the compound $(C_4H_9)_2Sn(SCH_2CH_2OOC\text{—}C_8H_{17})_2$.

If in the last-mentioned type of compound the aliphatic carboxylic acid radical is replaced by the radical of a sterically hindered phenol (alkane) carboxylic acid, it is to be expected that, in addition to their action as PVC stabilisers, the compounds will have an antioxidative action. It has however been found that, compared with the known fatty acid esters, the phenolic esters not only have an additional antioxidative action but also have a superior action in the thermal stabilisation of PVC. In comparison with the aforementioned known mercaptides of thioglycolic acid esters, the novel compounds of the invention are distinguished by better storage stability.

The present invention thus relates to compounds of the formula I or Ia $$\text{Me[SCH}_2\text{CH(R}^1)\text{—O—}\overset{\text{O}}{\underset{\|}{\text{C}}}\text{—(CH}_2)_m\text{—R}^2]_n \quad (I)$$

$$\text{Me[SCH}_2\text{CHCH}_2\text{—O—}\overset{\text{O}}{\underset{\|}{\text{C}}}\text{—(CH}_2)_m\text{—R}^2]_n \quad (Ia)$$
$$\underset{\overset{|}{\text{O—C—R}^3}}{\phantom{x}}$$
$$\underset{\overset{\|}{\text{O}}}{\phantom{x}}$$

wherein m is 0, 1 or 2, and n is an integer from 1 to 4, $R^1$ is hydrogen, $C_1$-$C_{10}$-alkyl, $$-CH_2-O-\overset{O}{\underset{\|}{C}}-(CH_2)_m-R^2, \quad -CH_2-O-\overset{O}{\underset{\|}{C}}-R^3$$

or $-CH_2OR^4$, $R^2$ is a group of the formula

[structure: phenol ring with $R^5$, $R^6$, OH]

$R^3$ is $C_1$-$C_{18}$-alkyl, $CH_3COCH_2$—, phenyl $COCH_2$—, phenyl,
$C_7$-$C_9$-phenylalkyl, vinyl or α-methylvinyl,
$R_5$ is $C_1$-$C_{18}$-alkyl, cyclohexyl or benzyl, $R^5$ and $R^6$ are $C_1$-$C_8$-alkyl, and Me is an n-valent metal, oxometal, alkoxymetal or organo-metal cation from the 1st to 5th group of the periodic system.

Compounds of the formula I are preferred.

Examples of mercaptide-forming cations Me are: $Na^+$, $K^+$, $Mg^{2+}$, $Ca^{2+}$, $Ba^{2+}$, $Zn^{2+}$, $Cd^{2+}$, $Al^{3+}$, $Sn^{4+}$, $R^7Sn^{3+}$, $(R^7)_2Sn^{2+}$, $(R^7)_3Sn^+$, $TiO^{2+}$, $(R^8O)_2Ti^{2+}$, $ZrO^{2+}$, $(R^8O)_2Zr^{2+}$, $VO^{3+}$ or $Sb^{3+}$, wherein $R^7$ is $C_1$-$C_{12}$-alkyl or phenyl, and $R^8$ is $C_1$-$C_{10}$-alkyl.

Me is preferably one of the cations selected from $Mg^{2+}$, $Ca^{2+}$, $Ba^{2+}$, $Zn^{2+}$, $R^7Sn^{3+}$, $(R^7)_2Sn^{2+}$ or $Sb^{3+}$, especially one of the cations $R^7Sn^{3+}$, $(R^7)_2Sn^{2+}$ or $Sb^{3+}$.

The radical $R^2$ is a sterically hindered phenol radical. Also the substituent $R^1$ can contain a sterically hindered phenol radical $R^2$. $R^1$ is however preferably hydrogen.

The index m can be 0, 1 or 2; it is however preferably 2. The alkyl groups $R^5$ and $R^6$ can be straight-chain or branched-chain, for example methyl, ethyl, isopropyl, tert-butyl, n-butyl, isoamyl, n-hexyl, 2-ethylhexyl or 1,1,3,3-tetramethylbutyl. Preferably at least one of the two radicals is a branched-chain alkyl group; particularly preferably however both radicals are tert-butyl, or one of the radicals is methyl and the other tert-butyl.

As alkyl, $R^1$, $R^3$, $R^4$, $R^7$ and $R^8$ can be straight-chain or branched-chain alkyl groups, such as methyl, ethyl, isopropyl, butyl, hexyl, 2-ethylbutyl, 2-ethylhexyl, n-octyl or n-decyl. $R^3$, $R^4$ and $R^7$ as alkyl can additionally be undecyl or dodecyl. $R^3$ and $R^4$ can also be higher alkyl, for example tetradecyl, hexadecyl or octadecyl. As phenylalkyl, $R^3$ can be for example benzyl, phenylethyl or phenylpropyl.

Examples of individual compounds of the formula I are the compounds of the following formulae (+ denotes therein t-butyl):

$$\text{Mg[SCH}_2\text{CH}_2\text{OOC—CH}_2\text{CH}_2\text{—}\phi\text{—OH]}_2$$

$$\text{Ca[SCH}_2\text{CH(CH}_3)\text{OOC—CH}_2\text{CH}_2\text{—}\phi\text{—OH]}_2$$

$$\text{Zn[SCH}_2\text{CHOOC—CH}_2\text{CH}_2\text{—}\phi\text{—OH]}_2$$
$$\underset{\text{C}_6\text{H}_{13}}{|}$$

$$\text{Sb[SCH}_2\text{CH}_2\text{OOC—}\phi(\text{CH}_3)\text{—OH]}_3$$

$$\text{Sn[SCH}_2\text{CH}_2\text{OOC—CH}_2\text{—}\phi\text{—OH]}_4$$

$$\text{ZrO[SCH}_2\text{CH—OOC—CH}_2\text{CH}_2\text{—}\phi\text{—OH]}_2$$
$$\underset{\text{CH}_2\text{OC}_8\text{H}_{17}}{|}$$

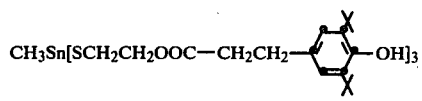

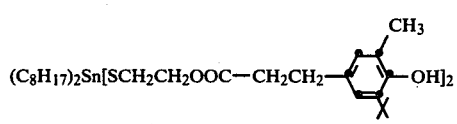

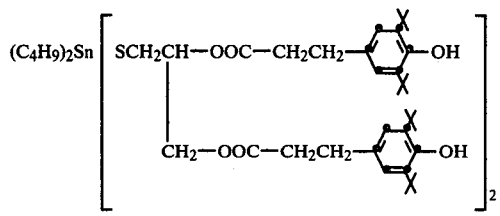

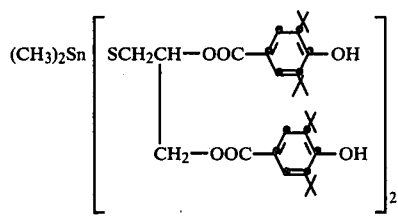

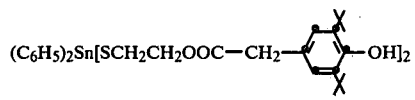

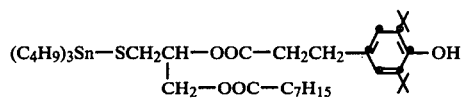

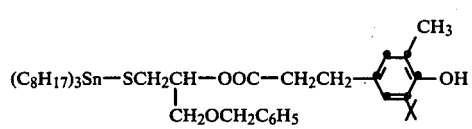

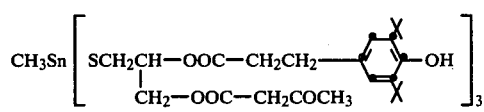

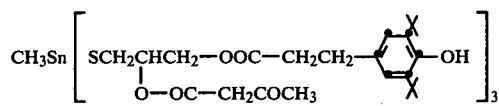

Examples of individual compounds of the formula Ia are compounds of the following formulae:

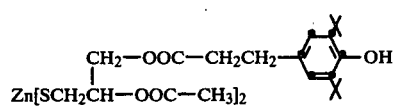

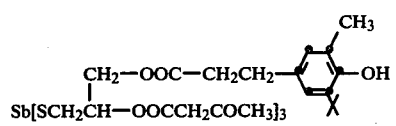

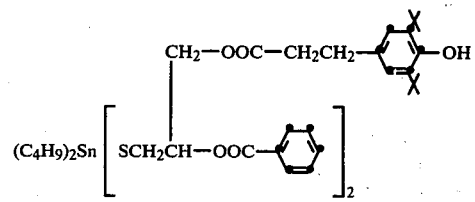

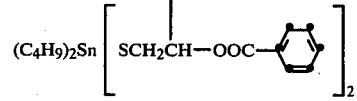

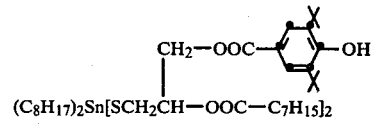

The metal mercaptides of the formula I can be produced from the corresponding mercaptans of the formula II $$HS-CH_2-CH(R^1)-OOC-(CH_2)_m-R^2 \quad (II)$$

by reaction with anhydrous metal chlorides of the formula $MeCl_n$ or with metal alcoholates $Me(OR^8)_n$, wherein $R^8$ is a $C_1$-$C_{10}$-alkyl group.

The metal mercaptides of the formula Ia can be produced in the same manner from the corresponding mercaptans of the formula IIa

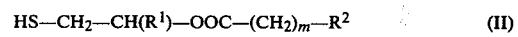

In the reaction of II or IIa with metal chlorides, there are added HCl acceptors, for example hydroxides, oxides, carbonates or amides of alkali metals or alkaline-earth metals, or tertiary amines, such as triethylamine, triethanolamine or pyridine. The reaction is preferably performed in an organic solvent in which the forming alkali chloride, alkaline-earth chloride or amine hydrochloride is difficultly soluble, in which however the metal mercaptide of the formula I is readily soluble, so that at the end of the reaction it can be easily separated from the chlorides by filtration. Examples of applicable solvents are hydrocarbons, such as benzene or xylene, chlorinated hydrocarbons, for example chloroform or methylene chloride, or ethers, such as diethyl ether, dibutyl ether, tetrahydrofuran or dioxane. Examples of metal chlorides which can be used for this purpose are: $ZnCl_2$, $CdCl_2$, $SnCl_4$, $CH_3SnCl_3$, $(C_8H_{17})_2SnCl_2$, $(C_4H_9)_3SnCl$, $VOCl_3$, $TiOCl_2$ or $SbCl_3$.

The reaction of II or IIa with metal alcoholates can be carried out with or without solvents, but it is preferably performed without solvents. The alcohol $R^8OH$ which forms can be continuously distilled off, by virtue of which the course of the reaction can be checked. Examples of alcoholates which can be used are: $NaOC_2H_5$, $KO-t-C_4H_9$, $Mg(O-i-C_3H_7)_2$, $Al(OC_4H_9)_3$, $C_8H_{17}Sn(OC_2H_5)_3$, $(C_4H_9)_2Sn(OC_4H_9)_2$, $Ti(OC_2H_5)_4$, $Zr(OC_3H_7)_4$ or $VO(OC_2H_5)_3$.

Some of the mercaptans of the formula II used as starting material are known and some are novel compounds.

Compounds of the formula II wherein $R^1$ is hydrogen or alkyl are described in the German Offenlegungsschrift No. 1,948,570. They can be produced by esterification of a mercaptoalkanol $HS-CH_2CH(R^1)-OH$ with a phenolic carboxylic acid $R^2—(CH_2)_m—COOH$ or with a derivative thereof, for example an alkyl ester or acid chloride.

Compounds of the formula II wherein $R^1$ is a radical $—CH_2—OOC—(CH_2)_m—R^2$ are novel compounds. They can be produced by esterification of 1-thioglycerin, $HS—CH_2—CH(OH)—CH_2OH$, with 2 equivalents of a phenolic carboxylic acid $R^2—(CH_2)_m—COOH$ or of an ester-forming derivative thereof. These compounds can also be used as stabilisers for organic materials.

Compounds of the formula II wherein $R^1$ is a radical $—CH_2—OOC—R^3$ or $—CH_2—OR^4$ are likewise novel compounds. They can be produced from glycidyl esters

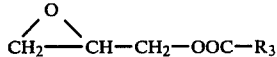

or from glycidyl ethers

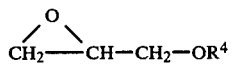

by reaction with $H_2S$ and subsequent esterification of the mercaptoalkanols with $R^2—(CH_2)_m—COOH$ or with an ester-forming derivative thereof.

The compounds of the formula IIa are likewise novel compounds. They can be produced from glycidyl esters of the formula

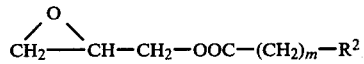

by reaction with $H_2S$ and subsequent esterification of the mercapto alcohols with $R_3—COOH$ or with an ester-forming derivative thereof.

The mercaptides of the formula I or Ia produced by the described processes are in the crude form oily, waxlike or solid materials. They are soluble in many organic solvents, for example in alcohols, in ketones or in dimethylformamide.

The compounds of the formulae I and Ia are usable as stabilisers for organic materials. This concerns all materials which can be damaged by thermal-oxidative ageing, for example fats, oils, waxes, lubricants, rubber, plastics or lacquers. They are applicable in particular for stabilising chlorine-containing thermoplasts, and elastomers and lubricants.

Chlorine-containing thermoplasts are for example polymers of vinyl chloride or of vinylidene chloride and copolymers thereof with monomers free from chlorine, also chlorinated polyolefins or chlorinated rubber. The stabilising of polyvinyl chloride (PVC) and of copolymers of vinyl chloride is of particular importance. These substrates can be suspension polymers, emulsion polymers or polymers produced by bulk polymerisation. Examples of vinyl chloride copolymers are in particular those with vinyl acetate. The PVC can be soft PVC or hard PVC. The stabilisation of hard PVC is preferred.

The addition of the compounds of the formula I or Ia to the chlorine-containing thermoplasts is made in an amount of 0.1 to 5 percent by weight, relative to the thermoplasts. The amount preferably used is 0.5-2 percent by weight.

Particularly suitable compounds for stabilising chlorine-containing thermoplasts are compounds of the formula I wherein Me is a cation $R^7Sn^{3+}$ or $(R^7)_2Sn^{2+}$.

Incorporation of the stabilisers into the polymeric substrates can be effected by the customary processes for incorporating additives into thermoplasts, for example by the mixing together of the constituents in powder form and subsequent moulding; or by addition of the stabilisers on a roll mill or in a kneading machine. There can be incorporated simultaneously other additives commonly used in the technology of chlorine-containing thermoplasts, for example lubricants, plasticisers, fillers, additives for increasing impact strength, pigments, light stabilisers and antioxidants, or further thermostabilisers. Examples of concomitantly used stabilisers are metal stearates and organic phosphites.

The stabilised chlorine-containing thermoplasts according to the invention can be moulded into shape by methods customarily used therefor, for example by means of extrusion, injection moulding or calendering, or by being processed as plastisols. An especially important field of application is the extrusion of sections and tubes.

The compounds of the formulae I and Ia can also be used as stabilisers for elastomers, where they act in particular as antioxidants. Examples of elastomers are natural rubber, polybutadiene, butadiene copolymers (such as styrene- or acrylonitrile-copolymers), polyisoprene, polychloroprene, butyl rubber, EPDM rubber, SBS- and SIS-block copolymers (thermoplastic elastomers), as well as mixtures thereof (polyblends) with each other or with other polymers.

Compounds particularly suitable for stabilising elastomers are the compounds of the formula I wherein Me is a cation $R^7Sn^{3+}$ or $(R^7)_2Sn^{2+}$.

The stabilising action of the compounds of the formula I or Ia on elastomers of the types mentioned is manifested by an increased resistance to degradation or discoloration during drying, storage and compounding of the crude elastomers, and also during the moulding into shape of the compound, and by a higher stability to ageing of the objects produced from the stabilised elastomers.

The amounts required for the stated purpose depend on the elastomer used and on the intended purpose of application. There is required in general 0.01 to 2 percent by weight of the stabiliser of the formula I or Ia, relative to the elastomer, particularly 0.05% to 0.5%.

Incorporation is effected by methods known with respect to rubber additives, preferably by addition in the dissolved form to the rubber solution, or in the emulsified form to the latex, after completion of polymerisation, or during compounding in the internal mixer or on the roll mill, optionally together with other stabilisers and rubber additives.

The compounds of the formulae I and Ia can also be used as lubricant additives. The lubricants can be lubricating oils or lubricating greases based on natural or synthetic oils. Of particular importance are the lubricating oils used for motor vehicles and aeroplanes.

The action of the compounds of the formulae I and Ia manifests itself in a lowering of wear and metal corrosion, and also in a stabilisation of the lubricant against oxidation, and hence in the extended service life of the lubricants stabilised therewith.

Depending on the desired effect, the amounts required for the stated purpose are 0.1 to 3 percent by weight of the compound of the formula I or Ia, relative to the amount of lubricant.

Compounds particularly suitable for stabilising lubricants are the compounds of the formula I wherein Me is a cation $R^7Sn^{3+}$.

The Examples which follow illustrate in detail the production and use of the compounds of the formula I. The term 'parts' denotes parts by weight, and temperature values are given in degrees Centigrade.

EXAMPLE 1

14 g of di-n-octyl-tin dichloride and 23.7 g of β-(3,5-ditert-butyl-4-hydroxyphenyl)-propionic acid-2-mercaptoethyl ester are dissolved in 100 ml of chloroform. There are then added portionwise, with gentle heating, 8.4 g of $NaHCO_3$, in the course of which $CO_2$ is evolved. The formed reaction water is subsequently removed by means of azeotropic distillation. The reaction solution is filtered and then concentrated in vacuo. The yield is 36.4 g of a yellow oil, which is the crude compound of the formula

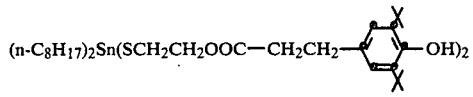

(Compound No. 1).

Analysis: Sn: calcuated 11.6%, found 11.3%; S: calculated 6.3%, found 6.2%.

The NMR spectrum agrees with the assumed structure.

The following compounds are produced in an analogous manner:

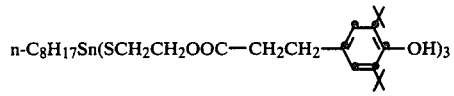

(Compound No. 2) glassy-brittle solid.

Analysis: Sn: calculated 9.5%; found 9.1%; S: calculated 7.0%, found 7.3%.

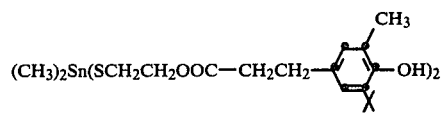

(Compound No. 3) highly viscous oil.

Analysis: Sn: calculated 16.0%, found 15.8%.

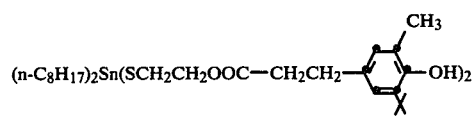

(Compound No. 4) highly viscous oil.

Analysis: Sn: calculated 12.7%, found 12.6%.

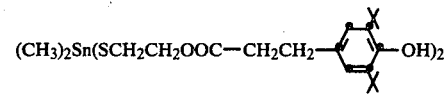

(Compound No. 5) glassy-brittle solid.

Analysis: Sn: calculated 14.4%, found 14.0%.

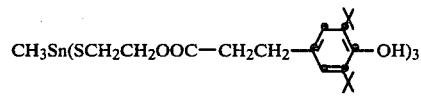

(Compound No. 6) glassy-brittle solid.

Analysis: Sn: calculated 10.4%, found 9.9%.

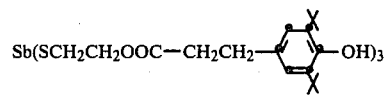

(Compound No. 7) glassy-brittle solid.

Analysis: Sn: calculated 10.7%, found 10.2%; S: calculated 8.5%, found 8.2%.

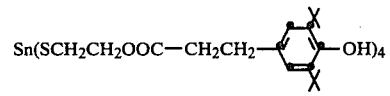

(Compound No. 8) oil

Analysis: Sn: calculated 8.1%, found 7.9%; S: calculated 8.7%, found 8.3%.

EXAMPLE 2

9.2g of anhydrous zinc chloride are suspended in 200 ml of tetrahydrofuran. To this suspension are added 20.2 g of triethylamine, and there is then added dropwise, with stirring, a solution of 47.4 g of β-(3,5-di-tert-butyl-4-hydroxyphenyl)-propionic acid-2-mercaptoethyl ester in 200 ml of tetrahydrofuran. The reaction mixture is refluxed for 8 hours. The major part of the chloroform is distilled off in vacuo, and 500 ml of diethyl ether are added to the residue. The amine hydrochloride which has precipitated is filtered off, and the filtrate is concentrated by evaporation to leave 49.6 g of the crude product of the formula

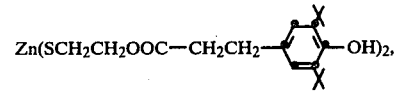

which has a wax-like consistency at room temperature (Compound No. 9).

Analysis: Zn: calculated 8.9%, found 8.4%; S: calculated 8.7%, found 8.3%.

The following compound is produced by the same method:

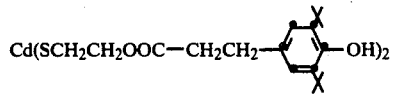

(Compound No. 10) wax-like solid.

Analysis: Cd: calculated 14.3%, found 13.9%; S: calculated 8.2%, found 7.9%.

EXAMPLE 3

8.2 of zirconium tetrapropylate and 16.9 g of β-(3,5-di-tert-butyl-4-hydroxyphenyl)-propionic acid-2-mercaptoethyl ester are heated, with stirring, at 150° for 1½ hours, in the course of which the formed ethanol is distilled off, and 3 g of distillate are obtained. The liquid reaction product is freed in vacuo from volatile constituents, and filtered through silica to obtain 20 g of a yellowish liquid, the NMR spectrum of which corresponds to the formula

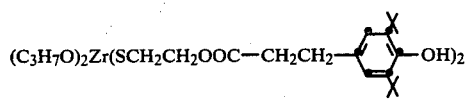

(Compound No. 11).

Analysis: Zr: calculated 10.3%, found 9.9%; S: calculated 7.3%, found 6.9%.

The following compounds are produced in an analogous manner:

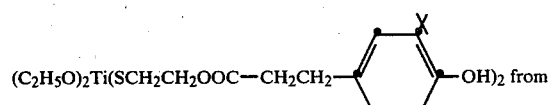

Ti(OC₂H₅)₄
(Compound No. 12) yellow liquid.

Analysis: Ti: calculated 5.9%, found 5.5%; S: calculated 7.9%, found 7.6%.

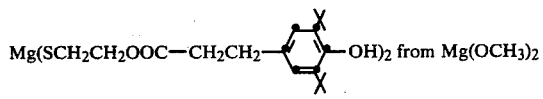

(Compound No. 13) yellowish liquid.

Analysis: Mg: calculated 3.5%, found 3.1%; S: calculated 9.2%, found 8.8%.

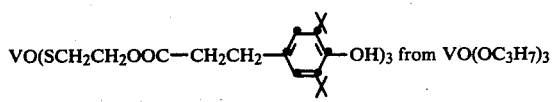

(Compound No. 14) glassy-brittle solid.

Analysis: V: calculated 4.7%, found 4.3%; S: calculated 8.9%, found 8.5%.

EXAMPLE 4

Thermostabilisation of PVC

| Recipe: |
|---|
| 100 parts of a commercial suspension PVC of K value 60, |
| 0.2 part of a montanic acid ester (Wax E, Hoechst AG), |
| 1.0 part of castor oil, and |
| 0.5 part of a stabiliser according to Table 1 |
| 101.7 . |

The constituents were homogenised on a two-roller mixing rolls at 180°, and subsequently rolled at 200°. A specimen was taken every three minutes and its discoloration measured by determination of the Yellowness Index (ASTM D 1925-70). The results are summarised in Table 1.

TABLE 1

| Employed stabiliser | Yellowness Index after | | | | | |
|---|---|---|---|---|---|---|
| | 3 min. | 6 min. | 9 min. | 12 min. | 15 min. | 18 min. |
| none | 12.6 | — | — | — | — | — |
| compound No. 2 | 4.8 | 6.0 | 7.8 | 9.3 | 12.6 | 22.6 |
| compound No. 7 | 10.5 | 13.3 | 16.0 | 22.7 | 97.7 | — |
| mixture of 0.5 parts of No. 5 and 0.4 parts of No. 6 | 5.0 | 8.6 | 13.4 | 44.3 | — | — |

EXAMPLE 5

Thermostabilisation of PVC 100 parts of a commercial suspension PVC having a K value of 60 (Vestolit S 6058, Chem. Werke A.G.) were homogenised at 180° on mixing rolls with 0.2 part of a montanic acid ester (Wax E, Hoechst A.G.) and 1.3 parts of the compound No. 5, and the mixture was rolled to form 0.3 mm thick sheets. The sheets were stored in a drying chamber at 180°. The Yellowness Index after 15 minutes was 9.4, after 30 minutes 11.3, after 45 minutes 14.9 and after 60 minutes 79.0.

EXAMPLE 6

Stabilisation of polybutadiene 100 parts of a commercial polybutadiene (having medium cis structures) were mixed at 50° with 0.2 part of a stabiliser on a 2-roller mixing rolls, and subsequently pressed out at 80°, in a hydraulic heating press, to form plates having a thickness of 10 mm and 2 mm, respectively.

(a) The 10 mm thick plates were aged at 80° in an air-circulation oven. A 5 g specimen was cut off each week, and its gel content was determined. For this purpose, the specimen was covered with 50 parts of toluene and shaken for 10 hrs. at room temperature. The resulting solution was filtered through a tared wire sieve (having a 0.044 mm sieve aperture), and the amount of gel remaining behind on the filter was dried and weighed, and the percentage amount relative to the weight-in specimen was calculated. Ageing was continued until a gel content of >5% was attained.

(b) An accurately weighed specimen of the 2 mm plate was kept for 30 minutes in silicone oil (Silikonöl AK 350, Wacker-Chemie, Munich) at 170°. The gel content was subsequently determined as under (a).

TABLE 2

| Employed stabiliser | (a) Ageing at 80°, time in weeks until gel content is >5% | (b) Ageing at 170°: gel content after 30 min. |
|---|---|---|
| none | 5 | 19.7% |
| compound No. 5 | 10 | 3.8% |
| compound No. 6 | 17 | 6.9% |

EXAMPLE 7

Addition to lubricating oil

1% of the compound No. 6 was added to a non-alloyed mineral lubricating oil. The compound dissolved in the oil after brief stirring at room temperature. 1% of triphenylthionophosphate (a commercial H.P. additive) was added to a comparative specimen. The specimens were tested according to DIN 51350, in the Shell four-ball apparatus, with respect to the following properties:

Weld load (WL)=load under which the balls weld together within 10 seconds (in kg).

Wear scar diameter (WSD)=mean wear diameter (in mm) under a load of 70 kg and 40 kg, respectively, for 1 hour.

TABLE 3

| Oil additive | WL (kg) | WSD (mm) |
|---|---|---|
| none | 160 | 1.1 |
| 1% of compound No. 6 | 200 | 0.4 |
| 1% of triphenylthionophosphate | 165 | 0.62 |

The compound No. 6 exhibited in oil also a satisfactory hydrolysis behaviour and a satisfactory copper- and iron-corrosion behaviour.

What is claimed is:

1. A compound of the formula I or Ia

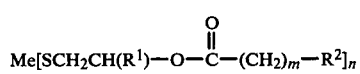

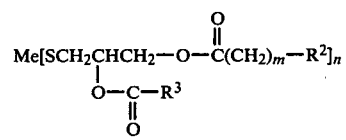

wherein m is 0, 1 or 2, and n is an integer from 1 to 4, $R^1$ is hydrogen, $C_1$-$C_{10}$-alkyl,

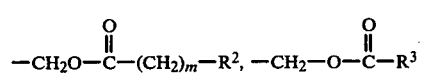

or —$CH_2OR^4$, $R^2$ is a group of the formula

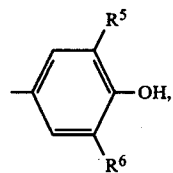

$R^3$ is $C_1$-$C_{18}$-alkyl, $CH_3COCH_2$—, phenyl $COCH_2$—, phenyl,
$C_7$-$C_9$-phenylalkyl, vinyl or $\alpha$-methylvinyl,
$R^4$ is $C_1$-$C_{18}$-alkyl, cyclohexyl or benzyl,
$R^5$ and $R^6$ are $C_1$-$C_8$-alkyl,
Me is the metal cation $Na^+$, $K^+$, $Mg^{2+}$, $Ca^{2+}$, $Ba^{2+}$, $Zn^{2+}$, $Cd^{2+}$, $Al^{3+}$, $Sn^{4+}$, $R^7Sn^{3+}$, $(R^7)_2Sn^{2+}$, $(R^7)_3Sn^+$, $TiO^{2+}$, $(R^8O)_2Ti^{2+}$, $ZrO^{2+}$, $(R^8O)_2Zr^{2+}$, $VO^{3+}$ or $Sb^{3+}$, $R^7$ is $C_1$-$C_{12}$ alkyl or phenyl, and $R^8$ is $C_1$-$C_{10}$alkyl.

2. A compound of the formula I or Ia according to claim 1, wherein Me is any one of the cations: $Mg^{2+}$, $Ca^{2+}$, $Ba^{2+}$, $Zn^{2+}$, $R^7Sn^{3+}$, $(R^7)_2Sn^{2+}$ or $Sb^{3+}$, and $R^7$ is $C_1$-$C_{12}$-alkyl or phenyl.

3. A compound of the formula I according to claim 2, wherein Me is any one of the cations: $R^7Sn^{3+}$, $(R^7)_2Sn^{2+}$ or $Sb^{3+}$, and $R^7$ has the meaning defined in claim 2.

4. A compound of the formula I according to claim 1, wherein $R^1$ is hydrogen, m is 2, $R^5$ is methyl or tert-butyl, and $R^6$ is tert-butyl.

5. A compound of any one of the following formulae according to claim 1:

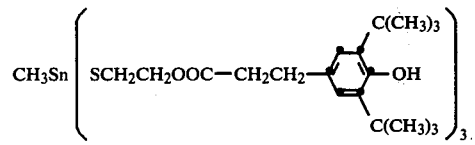

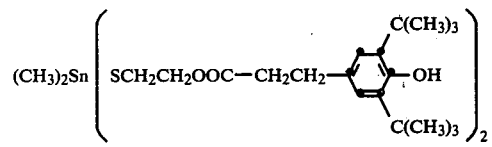

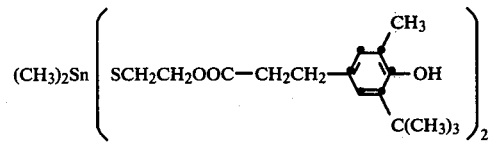

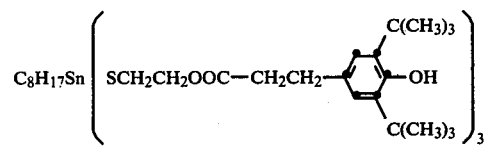

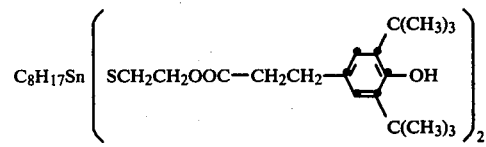

* * * * *